US00PP32822P2

(12) United States Plant Patent
Bedard

(10) Patent No.: US PP32,822 P2
(45) Date of Patent: Feb. 23, 2021

(54) GRANDIFLORA ROSE PLANT NAMED 'WEKSPODOTOGI'

(50) Latin Name: *Rosa hybrida*
Varietal Denomination: WEKspodotogi

(71) Applicant: Early Morning LLC, Lawrenceburg, IN (US)

(72) Inventor: Christian Bedard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 16/602,830

(22) Filed: Dec. 6, 2019

(51) Int. Cl.
*A01H 6/74* (2018.01)
*A01H 5/02* (2018.01)

(52) U.S. Cl.
USPC ..... Plt./141

(58) Field of Classification Search
USPC ..... Plt./141
See application file for complete search history.

(56) References Cited

U.S. PATENT DOCUMENTS

PP17,305 P2 12/2006 Carruth

OTHER PUBLICATIONS

HelpMeFind RosesClematis and Peonies. State of Grace Rose 2020.*
"'WEKabacima' Rose Description"; https://www.helpmefind.co/rose/pl.php?n=87276, 2 pages, accessed Mar. 2, 2020.

* cited by examiner

*Primary Examiner* — Annette H Para
(74) *Attorney, Agent, or Firm* — McKee, Voorhees & Sease, PLC

(57) ABSTRACT

A new variety of Grandiflora rose suitable for garden decoration, having flowers of soft gold with dark pink reverse coloration.

1 Drawing Sheet

Classification: The present invention relates to a new *Rosa hybrida* plant.

Variety denomination: The new plant has the varietal denomination 'WEKspodotogi'.

BACKGROUND OF THE INVENTION

This invention relates to a new and distinct variety of Grandiflora Rose. It was discovered in the summer of 2011 in Wasco, Calif. as a mutation of the variety known as 'WEKabacima' (not patented).

SUMMARY OF THE INVENTION

Among the features which distinguish the new variety from other presently available and commercial rose cultivars known to the inventor are the following combinations of characteristics: its unusual soft gold with dark pink reverse flower coloration, its abundant blooms, its excellent color stability throughout the life of the flowers and its numerous hairs on the peduncle. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKspodotogi' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from the cultivar of origination, 'WEKabacima' by the following combination of characteristics: whereas 'WEKspodotogi' bears medium to somewhat large flowers (about 7.4 to about 10.7 cm. in diameter) of soft gold with dark pink reverse coloration, 'WEKabacima' bears significantly larger flowers (about 12.0 to about 14.0 cm. in diameter) of coral-pink with an coral orange heart coloration. The flowers of the new variety have a moderate fruity fragrance, whereas the flowers of the cultivar of origination have no distinguishable fragrance.

COMPARISON WITH THE CLOSEST COMMERCIALLY AVAILABLE CULTIVAR

The new variety may be distinguished from its closest commercially available cultivar, 'WEKosupalz' (U.S. Plant Pat. No. 17,305) by the following combination of characteristics: whereas 'WEKspodotogi' bears very double flowers (about 31 to 112 petals) of soft gold with dark pink reverse coloration, 'WEKosupalz' bears double flowers of golden orange coloration with a bronzy red reverse with significantly lesser petalage (about 26 to 30 petals). The new variety has an upright moderately spreading medium height growing habit (about 102 to about 135 cm. in height), whereas the closest commercially available cultivar has a very upright significantly taller growing habit (about 170 to about 200 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong medium to somewhat long stems (about 22 to about 95 cm.). The cluster ranges from about 12.5 to about 14.5 cm. in diameter. Outdoors, the plant blooms abundantly and nearly continuously during the growing season. The flowers have a moderate fruity fragrance.

BUD

The peduncle is about 1.1 to about 4.5 cm. in length, of average caliper (about 0.2 to about 0.4 cm. in diameter), and usually erect. It is smooth with numerous hairs. Peduncle color is between 146C and 146D sometimes lightly suffused, especially on the side exposed to the sun, with between 187A and 187B.

Before the calyx breaks, the bud is about 1.2 to about 1.9 cm. in diameter at the widest point, about 1.3 to about 2.2 cm. in length, and moderately ovoid to somewhat pointed in shape. The surface of the bud bears between 6 to 8 foliaceous appendages with many hairs, usually with slender entire foliaceous parts extending beyond the tip of the bud about ¾ or more of its length. Bud color is between 137C and 138A often moderately suffused, especially on the side exposed to the sun, with between 187A and 187B.

The sepals are 5 per flower, about 2.2 to about 4.1 cm. in length and about 0.6 to about 1.1 cm. in width at the widest point. The outer surface color of the sepal is between 137C and 138A often moderately suffused, especially on the side exposed to the sun, with between 187A and 187B. The outer surface of the sepal is smooth and bears between 0 to 4 foliaceous appendages with many hairs. The inner surface color of the sepal is near 146D broadly bordered by near 137B. After the sepals open, the inner surface color is often heavily suffused, especially on the area exposed to the sun, with between 187A and 187B. The inner surface of the sepal is covered with fine wooly tomentum; sepal margins are entire and lined with very few stipitate glands and numerous hairs. The sepals are moderately permanent, and usually straight in shape with acute apices.

The receptacle of the flower is of medium length (about 0.4 to about 1.0 cm.) and average to somewhat heavy in caliper (about 0.7 to about 1.2 cm. in diameter). The receptacle is urn-shaped in form. Its surface is smooth with few hairs and with moderately thick fleshy walls. The receptacle color is between 144A and 138A sometimes lightly suffused with between 187A and 187B.

As the petals open (after the calyx breaks), the bud is about 1.6 to about 2.4 cm. in diameter at the widest point, about 1.8 to about 2.5 cm. in length, and pointed to somewhat ovoid in form. The color of the under surfaces of the newly opened petals is between 53B and 53C often heavily blushed on the outermost petals with between 53A and 60A to as dark as between 187A and 187B. At the point where the petal attaches, there is a somewhat large zone of near 145C. The color of the upper surfaces of the newly opened petals is between 154D and 2C. There is no visible change in coloration at the point where the petal attaches.

BLOOM

When fully open, the bloom ranges from about 7.4 to about 10.7 cm. in diameter. Petalage is very double with about 31 to 112 petals and about 3 to 19 petaloids irregularly arranged. When partially open, the bloom form is moderately globular to cupped, and the petals are moderately tightly spiraled to cupped with petal edges somewhat reflexed outward. When fully open, the bloom form is more cupped, and the petals are loosely cupped to sometimes somewhat folded laterally with petal edges somewhat reflexed outward.

PETALS

The substance of the petals is heavy and of moderately thick thickness, with upper surfaces slightly satiny to somewhat shiny and under surfaces slightly shiny. The petals are about 2.5 to about 5.5 cm. in length and about 0.9 to about 5.6 cm. in width at the widest point. Petal margins are entire.

The outer petals are broadly obovate in shape with rounded to sometimes somewhat mucronate apices.

The inner petals are broadly oblanceolate in shape with rounded to sometimes somewhat mucronate apices.

Petaloids are about 1.1 to about 4.1 cm. in length and about 0.7 to about 2.2 cm. in width at the widest point. Petaloids are irregularly shaped moderately oblanceolate to somewhat subulate with rounded to moderately lacerated apices.

NEWLY OPENED FLOWER

The under surface color of the outer petals is between 54A and 54B sometimes moderately blushed with between 53A and 60A. At the point where the petal attaches, there is a somewhat small zone of between 150C and 154C. The color at the base of the upper surfaces of the outer petals is between 13C and 14C gradually suffusing toward the middle of the petal to between 19B and 27C. There is no visible change in coloration at the point where the petal attaches.

The under surface color of the intermediate and inner petals is between 51A and 54B. The color at the base of the upper surfaces of the intermediate and inner petals is between 13C and 14C gradually suffusing toward the middle of the petal to between 19B and 20B.

The under and upper surface colors of the petaloids are similar in coloration to the upper and under surfaces of the intermediate and inner petals.

The general tonality of the newly opened flower is between 19B and 20B.

THREE-DAY-OLD FLOWER

The color at the base of the under surfaces of the outer petals is between 10C and 11B gradually suffusing toward the middle of the petal to between 66D and 68D. There is no visible change in coloration at the point where the petal attaches. The color at the base of the upper surfaces of the outer petals is between 11B and 10B gradually suffusing toward the middle of the petal to between 36D and 155C. There is no visible change in coloration at the point where the petal attaches.

The color at the base of the under surfaces of the intermediate and inner petals is between 10C and 11B gradually lightly suffusing toward the middle of the petal to between 66D and 69A. The color at the base of the upper surfaces of the intermediate and inner petals is between 11B and 10B gradually suffusing toward the middle of the petal to between 18C and 19C.

The under and upper surface colors of the petaloids are similar in coloration to the upper and under surfaces of the intermediate and inner petals.

The general tonality of the three-day-old flower is between 18C and 19C.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 85) and are arranged regularly about the pistils; a few are mixed with petaloids. The filaments are of somewhat short to medium length (about 0.3 to about 0.9 cm.) most with anthers. Filaments are between 4C and 2C in color. The anthers are moderately small for the class and all open approximately at the same time. Anther color when immature is near 21B on the external part and near 8D on the internal part. Anther color at maturity is near 163A on the external part and near 200A on the internal part. Pollen is somewhat sparse and between 18B and 16D in color.

FEMALE REPRODUCTIVE ORGANS

Pistils vary in number (average about 95). The styles are moderately even, somewhat long in length (about 0.5 to about 1.0 cm.), moderately thin in caliper and loosely bunched. Stigma color is between 11B and 10B. Style color is between 149D and 145D often moderately suffused near the top with between 53B and 53C. Ovaries are usually all enclosed in the calyx. The ovaries are small and between 158A and 158B in color.

Hips are of average to somewhat long length (about 1.4 to about 2.5 cm.), flat at the top and moderately globular in form, and between 31A and 33B in color when ripe. The hip surface is smooth with few hairs and with thick fleshy walls.

The seeds are irregularly rounded, smooth in texture, approximately 11 to about 26 per hip, about 0.4 to about 0.7 cm. in diameter at the widest point and between 164B and 164C in color.

FOLIAGE

The compound leaves are usually comprised of three to seven leaflets and are borne abundantly. The seven-leaflet leaves are about 10.0 to about 16.5 cm. in length and about 6.7 to about 12.0 cm. in width at the widest point, moderately crisp to somewhat leathery in texture on both sides, and semi-glossy in finish on the upper side and matte in finish on the under side. The leaves have a pinnate venation pattern. The terminal leaflets are about 4.8 to about 8.0 cm. in length and about 2.5 to about 4.8 cm. in width at the widest point, shaped moderately ovate to somewhat oval with acute to somewhat acuminate apices and rounded to somewhat acute bases. Their margins are usually simply serrate.

The upper surface color of the mature leaf is between 137A and 139A. The under surface color of the mature leaf is near 147B. The under and upper colors of the leaf veins on the mature leaf are similar in coloration to the upper and under surfaces colors of the mature leaf. The upper surface color of the young leaf is between 137B and 137C, often heavily suffused with between 187A and 187B. The under surface color of the young leaf is between 138B and 146C, often heavily suffused with between 187B and 187A. The under and upper colors of the leaf veins on the young leaf are similar in coloration to the upper and under surfaces colors of the young leaf.

The rachis is about 5.3 to about 9.3 cm. in length, about 0.1 to about 0.15 cm in width at the widest point, and rough. The upper side is deeply grooved with many hairs and few stipitate glands on the edges of the grooves. The under side of the rachis is rough with many hairs, some stipitate glands and few small prickles. The rachis color is near 145A on the under side and near 146C on the upper side, often moderately suffused on the young leaves with between 187B and 187C.

The stipules are about 1.1 to about 2.3 cm. in length and of medium width (about 0.4 to about 0.9 cm.) with moderately long straight points that usually turn out at an angle of more than 45 degrees and sometimes recurve toward the stem. The under and upper surface color of the stipule is between 137A and 137B. The upper and under surfaces of the stipules are smooth in texture.

The petiole is somewhat light to average in caliper and rough. The upper side is deeply grooved with many hairs and few stipitate glands on the edges of the grooves. The under side of the petiole is rough with many hairs, some stipitate glands and few small prickles. The petiole is about 0.5 to about 1.3 cm. in length and about 0.1 to about 0.15 cm in width at the widest point. The petiole color is near 145A on the under side and near 146C on the upper side, often moderately suffused on the young leaves with between 187B and 187C.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has an upright moderately spreading medium height growing habit (about 102 to about 135 cm. in height and about 112 to about 122 cm. spread at the widest point), with very full branching. It displays vigorous growth and the canes are of moderately heavy caliper for the class (about 1.3 to about 3.7 cm. in diameter at the widest point).

The color of the major stems is between 137C and 146A. The major stems are rough in texture and they bear many large prickles that are about 0.5 to about 1.1 cm. in length. The large prickles are angled moderately downward with a medium length somewhat broad oval base; prickle color is between 164B and 165C often moderately suffused with between 201C and 201D. The major stem bears many small prickles of similar shape and coloration.

The color of the branches is between 146B and 137C. The branches are rough in texture and they bear many large prickles which are of similar size and shape to the large prickles on the major stems; prickle color is near 161A. The branches bear many small prickles of similar shape and coloration.

The color of the new shoots is between 146C and 137C sometimes lightly suffused with between 187B and 187C. The new shoots are rough in texture and they bear many large prickles which are of similar shape to the large prickles on the major stems. The prickles are about 0.5 to about 0.7 cm. in length. Prickle color is between 152C and 152D usually moderately suffused with between 187C and 187D. The shoots bear many small prickles of similar shape and coloration.

I claim:

1. A new and distinct Grandiflora rose plant of the variety substantially as described and illustrated herein.

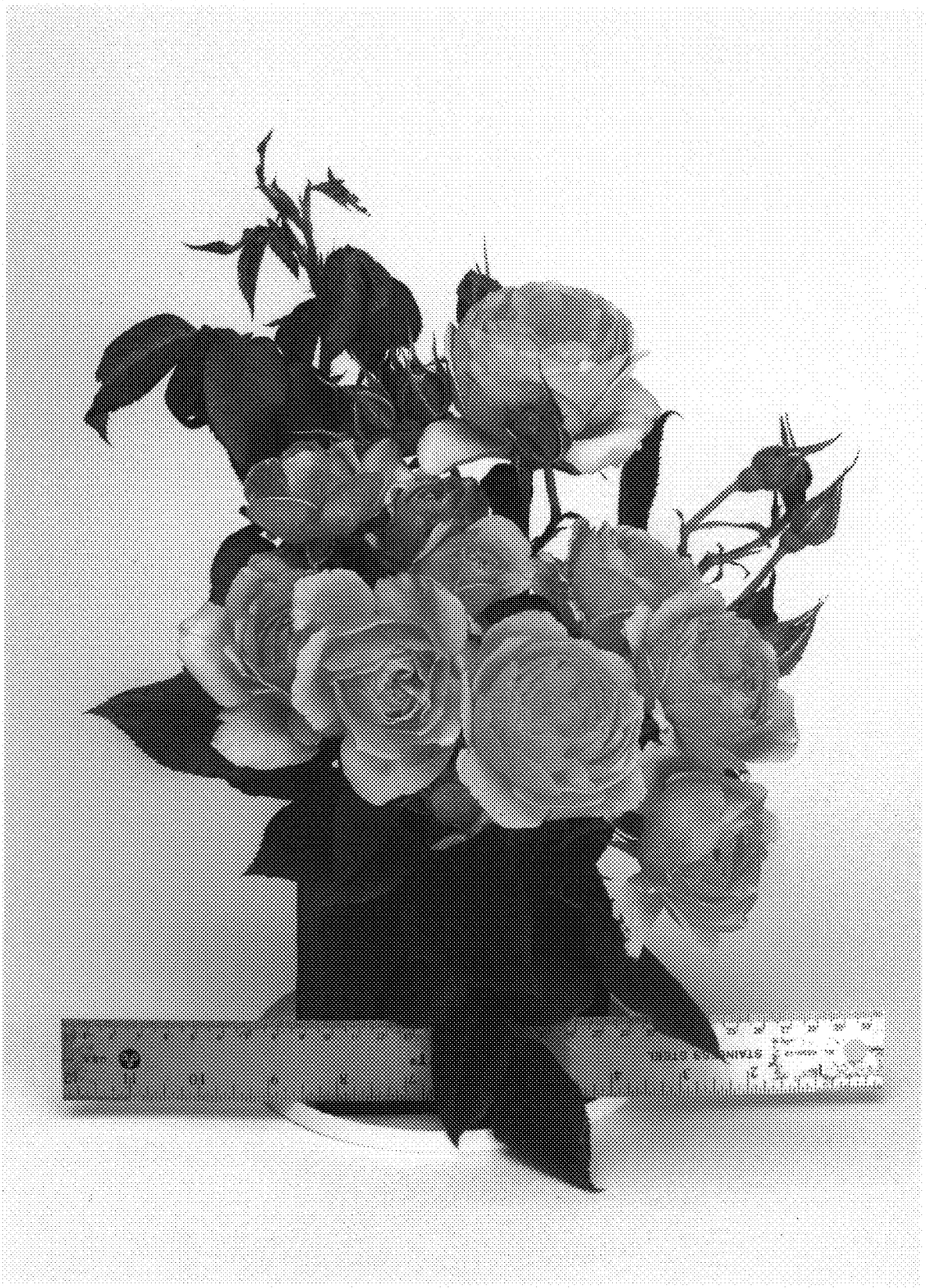

* * * * *